(12) United States Patent
Sacherer (10) Patent No.: US 6,497,845 B1
(45) Date of Patent: Dec. 24, 2002

(54) STORAGE CONTAINER FOR ANALYTICAL DEVICES

(75) Inventor: Klaus-Dieter Sacherer, Kirchheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/298,689

(22) Filed: Apr. 23, 1999

(30) Foreign Application Priority Data

Apr. 24, 1998 (DE) .......................... 198 18 359
Nov. 25, 1998 (DE) .......................... 198 54 316

(51) Int. Cl.⁷ ........................... B01L 3/00; G01N 37/00
(52) U.S. Cl. .................. 422/104; 422/58; 422/102; 221/25; 221/79; 221/87; 206/569
(58) Field of Search .................. 422/58, 61, 93, 422/102, 82.05, 104; 436/43, 46, 48, 164; 221/79, 88, 25, 87; 206/569

(56) References Cited

U.S. PATENT DOCUMENTS

| | | | | |
|---|---|---|---|---|
| 4,494,902 A | * | 1/1985 | Kuppens et al. ............ 414/223 |
| 4,943,415 A | * | 7/1990 | Przybylowicz et al. ....... 422/56 |
| 5,332,549 A | * | 7/1994 | MacIndoe, Jr. .............. 422/63 |
| 5,405,011 A | * | 4/1995 | Haber et al. ................. 206/531 |
| 5,489,414 A |   | 2/1996 | Schreiber et al. ............. 422/64 |
| 5,505,308 A | * | 4/1996 | Eikmeier et al. ........... 206/449 |
| 5,510,266 A |   | 4/1996 | Bonner et al. ................ 436/43 |
| 5,534,225 A | * | 7/1996 | Seto et al. ................... 221/197 |
| 5,564,593 A | * | 10/1996 | East, Sr. ........................ 221/3 |
| 5,611,996 A | * | 3/1997 | Shaw et al. ................... 422/64 |
| 5,738,244 A | * | 4/1998 | Eikmeier et al. ............ 422/102 |
| 5,759,010 A | * | 6/1998 | Jacobs et al. ............. 414/796.8 |
| 5,971,941 A | * | 10/1999 | Simons et al. ............... 600/573 |
| 6,136,270 A | * | 10/2000 | Maes et al. .................... 422/64 |
| 6,136,274 A | * | 10/2000 | Nova et al. .................. 422/102 |

FOREIGN PATENT DOCUMENTS

| | | | |
|---|---|---|---|
| DE | 197 53 847 A1 | 6/1999 | ............. B01L/3/00 |
| EP | 0 138 152 B1 | 12/1988 | .......... G01N/21/03 |
| EP | 0 565 970 A1 | 10/1993 | ............. A61B/5/14 |
| EP | 0 622 119 A1 | 11/1994 | ............. B01L/9/00 |
| EP | 0 630 609 A2 | 12/1994 | ............. A61B/5/14 |
| EP | 0 732 590 A2 | 9/1996 | .......... G01N/35/00 |
| EP | 0 738 666 A2 | 10/1996 | .......... B65D/83/04 |
| EP | 0 821 233 A2 | 1/1998 | .......... G01N/33/52 |
| EP | 0 821 234 A2 | 1/1998 | .......... G01N/33/52 |
| EP | 1022565 A2 | * 7/2000 | .......... G01N/33/48 |
| WO | WO 97/02487 | 1/1997 | ......... G01N/27/327 |

* cited by examiner

Primary Examiner—Jill Warden
Assistant Examiner—Kathryn Bex
(74) Attorney, Agent, or Firm—Richard T. Knauer; Jill L. Woodburn (57) ABSTRACT

A storage container for holding analytical devices, the storage container being made of a rigid material and containing separate chambers in each of which at most one analytical device can be accommodated, wherein the chambers are in a regular geometric arrangement in relation to one another and each of the chambers has at least two opposite openings each sealed by a foil, wherein at least one of the chambers comprises a means for fixing the position of an analytical device in the chamber. In addition the invention concerns a system for storing analytical devices containing a storage container according to the invention and two or more analytical devices.

7 Claims, 5 Drawing Sheets

STORAGE CONTAINER FOR ANALYTICAL DEVICES

BACKGROUND AND SUMMARY OF THE INVENTION

The invention concerns a storage container made of a rigid material for two or several analytical devices in which these can be accommodated individually chambers which are located with respect to one another in a regular geometric arrangement wherein each of the chambers has at least two opposite openings which are sealed by a foil. The invention also concerns a system for storing analytical devices containing a storage container according to the invention and two or several analytical devices.

Carrier-bound rapid tests have been established in specialised laboratories for the chemical and biochemical analysis of solid and liquid sample materials and also in particular for use outside permanent laboratories. Despite the often complex reactions involving sensitive reagents, such carrier-bound rapid tests that are based on a specially developed dry chemistry are simple and uncomplicated and can even be carried out by layman. The most prominent example of carrier-bound rapid tests are test strips for determining the content blood glucose in diabetics. Single or multizone test strips for urine analysis and diverse indicator papers are also known. Since other forms of carrier-bound rapid tests exist in addition to rapid tests in a strip form (test strips), they are generally referred to as "analytical test elements".

Dry chemical carrier-bound rapid tests are usually multiply packaged for sale to the end user. The rapid test is usually in a first package which directly surrounds it (primary packaging) which is in turn placed in a further package (external packaging, secondary packaging) which, in addition to the primary packaging, usually contains handling instructions for rapid tests in the form of package inserts. The primary packaging is designed to fulfil the essential functions of maintaining the function of the chemical and biochemical components on the test element during a long period of storage. These functions are above all protection from the influence of light rays, protection from the ingress of atmospheric humidity, dirt, germs and dust as well as protection from mechanical impairment of the test elements.

One of the most frequently encountered forms of primary packaging is to offer test elements that have been loosely loaded into aluminium or plastic tubes which are sealed by a stopper that is pressed on or screwed on. The functions of the primary packaging mentioned above are satisfactorily fulfilled by these tube packages. These appear to be outmoded due to the complicated manual removal of individual test elements from the primary packaging which is why alternative packaging concepts have been developed. In addition to the aforementioned properties these additionally enable the test elements to be individually and automatically removed from the packaging and made directly available to a measuring instrument which measures and subsequently evaluates the test results.

EP-A 0 622 119 describes storage systems made of stiff, water-vapour-tight materials for strip-like test elements in which the test elements are individually stored in foil-sealed chambers (individual sealing). The chambers for the test strips—which is another term for strip-like test elements—are in the shape of tubes with a rectangular cross-section and which are oriented relative to one another in a geometric and regular manner resulting in the storage system being in the form of an essentially rectangular magazine or hinged case both having parallel chambers lying next to one another in one line or in the shape of an elongate cylinder or a flat circular disk with chambers grouped radially around a central axis. The test elements can be removed from the storage system either manually or by a mechanical device and the test elements remaining in the storage container continue to be protected by individual sealing. In addition EP-A 0 622 119 describes the possibility of providing desiccants for the test strips such as silica gels and molecular sieves within the chambers in order to absorb residual moisture resulting from the manufacturing process for the test strips or which has penetrated into the chambers despite the sealing and use of materials that are impermeable to water vapour. A data carrier can be attached to one of the outer sides of the storage system such as e.g. a label in readable type, a bar code label or a magnetic strip on which batch-specific data and optionally further information on the test elements in the system is stored and can be recalled. Some of the storage containers for test elements described in EP-A 0 622 119 are suitable for use in appropriately designed measuring systems composed essentially of a measuring instrument, storage container and test elements.

EP-A 0 732 590 and U.S Pat. No. 5,489,414 describe round, disk-shaped storage containers for test elements which are suitable for use in compact measuring instruments for example for blood sugar self-monitoring by diabetics. In this case the test elements are arranged radially in one plane around the centre of the disk and are individually sealed dirt-tight and moisture-tight in blisters such as those that are known for individually packaging tablets. A separate blister for a desiccant is provided for each test element in the storage container according to EP-A 0 732 590 and the desiccant blister and test element blister are linked together to ensure an effective desiccation of the test element blister.

Cylindrical test element magazines manufactured from plastic in an injection molding process are known from U.S. Pat. No. 5,510,266 and EP-A 0 738 666 in which the individual test elements are arranged similar to cartridges in a revolver cylinder in continuous chambers extending from the base of the cylinder to the opposite cover surface. As already described further above for EP-A 0 622 119, the test elements in this case are individually sealed into parallel, elongate, tube-shaped chambers arranged radially around a central longitudinal axis for which the circular base and cover surfaces of the cylindrical storage container are sealed with foils such as aluminium foil. In order to remove the test elements from the magazine, one of the sealing foils is pierced with a plunger and the test element to be removed is pushed out of its chamber through the opposite sealing foil and is thus made available for its intended use. Like EP-A 0 732 590 each test element chamber is provided with a separate desiccant chamber which is linked to the test element chamber via a channel so that the test element chamber can be reliably dehumidified by the desiccant. The test element magazines from U.S. Pat. No. 5,510,266 and EP-A 0 738 666 are also mainly designed for use in compact measuring instruments.

The storage containers described in the prior art have the disadvantage that the test elements are not optimally protected against environmental influences and in particular mechanical influences. The blister packages for test elements described in EP-A 0 732 590 and U.S. Pat. No. 5,489,414 are manufactured from relatively thin plastic foils and by their nature provide only an inadequate protection of the test elements against mechanical damage for example by unintentional pressing or bending the packaging. The test element storage containers from U.S. Pat. No. 5,510,266 and EP-A 0 738 666 provide better protection in this case since they are made of rigid solid materials which at least offer more resistance to pressure and bending stress than blister packages. However, the mechanical weak points of the drum-shaped packaging type disclosed in U.S. Pat. No. 5,510,266 and EP-A 0 738 666 are the sealing foils which seal the base and covering surfaces of the cylindrical drum in order to in this manner produce sealed test element chambers. These sealing foils are usually made of thin foils such as aluminium foils in order that they can be easily pierced when the test elements are removed and are easily damaged when the package is unintentionally dropped or not carefully placed on a support. Since slight openings in the sealing foil can already allow a penetration of dust, germs and atmospheric humidity into the test element chambers, this can result in serious damage to the test elements that are to be protected by the packaging.

A further disadvantage of the storage containers described in the prior art is that the automatic removal of test elements for example with the aid of a plunger often leads to a canting of the test elements in their chamber. Consequently these systems are not sufficiently reliable for dispensing test elements.

The described disadvantages of the packaging concepts for test elements also essentially apply to other analytical devices such as lancets or sampling elements. Although the latter devices usually contain no sensitive reagents that have to be protected against environmental influences, in these cases attention must also be paid to sterile conditions in the chambers of the storage container so that the stored elements do not become unusable on longer storage.

The object of the invention is to eliminate the disadvantages of the prior art. In particular it is an object of the present invention to provide a compact storage container for analytical devices i.e. test elements, sampling elements and lancets that can be manufactured cheaply and in large numbers and which can reliably protect the analytical devices located therein against damaging environmental influences such as light, moisture or mechanical influences. Furthermore it should be possible to integrate the storage container into an analytical system comprising a compact measuring instrument, the storage container and test elements and enable a reliable, i.e. faultless, removal of the analytical devices.

The invention concerns a storage container made of a rigid material for two or several analytical devices containing separate chambers in each of which at most one device can be accommodated wherein the chambers are in a regular geometric arrangement in relation to one another and each of the chambers has at least two opposite openings each sealed by a foil wherein each chamber has means for fixing the position of the analytical devices in the chamber.

The term "analytical devices" is understood to include analytical test elements, cuvettes, pipettes or lancets. They are preferably analytical test elements or lancets and particularly preferably analytical test elements. Analytical test elements in the sense used here are test strips that can be evaluated visually or optically by means of an apparatus, electrochemical sensors etc. Since such analytical devices are comprehensively described in the prior art and are familiar to a person skilled in the art in a multitude of embodiments, a detailed description is unnecessary here. Reference is for example made to the following documents: German Patent Application file number 197 53 847.9, EP-A 0 138 152, EP-A 0 821 234; EP-A 0 821 233, EP-A 0 630 609, EP-A 0 565 970 and WO 97/02487.

The form, function and materials of the storage container according to the invention largely correspond to the prior art. EP-A-0 622 119, EP-A-0 738 666 and U.S. Pat. No. 5,510, 266 are in particular mentioned. Explicit reference is made here to these documents.

The storage container according to the invention has particularly preferably the form of an essentially cylindrical, elongate drum in which chambers for holding the analytical devices are arranged radially around the longitudinal axis. The height of the drum essentially depends on the length of the analytical devices that have to be accommodated. The base and cover surfaces of the cylindrical container contain the openings of the chambers which are tightly sealed with foil. All openings of a surface are preferably sealed individually and independently of one another but, however, using only one piece of foil. The individual and independent sealing ensures that when one chamber is opened the sealing foils for the remaining chambers are not damaged.

The main body of the storage container according to the invention is preferably made of a rigid injection moldable plastic such as polyethylene or polypropylene. The foil for sealing the chamber openings which is also referred to as sealing foil is preferably made of aluminium or an aluminium-plastic laminate and is tightly bonded to the main plastic body of the storage container by known processes such as welding or glueing. The sealing foil is preferably fixed to the injection molded body by means of hot-melt adhesive. In order to prevent adhesive remnants from protruding into the device chambers or beyond the rim of the storage container, areas for receiving adhesive remnants can be provided in a preferred embodiment of the storage container according to the invention on individual or all affected edges. For example a circumferential recess can be present on all effected edges to receive the adhesive remnants.

In a preferred embodiment of the storage container according to the invention an individual store of desiccant is provided for each chamber for analytical devices which is preferably accommodated in a separate desiccant chamber. In principle all desiccants obtainable as solids or pasty masses can be used as desiccants, in particular, silica gel, molecular sieve and similar materials. The desiccant chamber is dimensioned according to the amount of desiccant that is required to desiccate the device chamber. The desiccant chamber and device chamber are in a contact enabling gas exchange. They are preferably connected to one another by a channel which allows air exchange between the chambers and thus a desiccation of the device chamber. The size and geometry of the channel are preferably such that the desiccant, for example silica gel and molecular sieve, cannot enter the device chamber. If necessary the size of the desiccant particles must be chosen accordingly.

The desiccant chamber preferably contains two openings one of which is used to fill the chamber with desiccant (feed inlet) and the other provides the contact enabling gas exchange with the chamber for the analytical device (channel opening). Whereas the channel opening must remain open at all times in order to enable a desiccation of the device chamber, the feed inlet of the desiccant chamber can be sealed after loading with desiccant. This can prevent an unintentional escape of the desiccant from the chamber for example in subsequent manufacturing or filling steps of the storage container according to the invention. The feed inlet of the desiccant chamber can preferably be sealed by covering for example with cardboard, paper, plastic or metal foil. In addition it is preferable to cover the feed inlet by a plastic or adhesive plug. The feed inlet of the desiccant chamber is particularly preferably sealed by corking injection molding material from the rim area of the opening with the aid of a suitable tool i.e. is pushed into the opening and thus forms a cover for the opening.

A difference to the known storage containers for analytical devices in the prior art which is essential for the invention is that a means for fixing the position of the analytical device in the chamber is provided in each chamber which serves to hold an individual analytical device. The fixing of the analytical device in the chamber surprisingly turned out to be advantageous since this prevents damage to the foil which makes an individual seal to the chambers and thus also prevents penetration by humidity, dust, dirt and germs. When the storage container is unintentionally dropped, shaken or knocked, the sealing foil may be perforated by the analytical device in the storage container described in the prior art in which the analytical devices are loose and can therefore move within the chambers. With these containers, it is not possible to ensure a reliable sealing of the individual chambers during manufacture, storage, transport and use of the storage container, and thus, the analytical devices in the chambers cannot be reliably protected. The introduction according to the invention of means for fixing the position of the analytical devices within the respective chamber solves this problem. Fixing the analytical device in its chamber largely prevents unintentional perforation of the sealing foil of the chamber by the analytical device.

Different designs are possible according to the invention as a means for fixing the analytical devices in a fixed position in a chamber. In addition to fixing the position of the analytical devices in the chamber in a stable manner, these means must, however, allow the analytical device to be easily loaded into the chamber and be removed from this again when required for use.

A preferred means for fixing the analytical devices in a fixed position in the chamber has proven to be a partial narrowing of the chamber preferably in that region of the chamber which is opposite to the removal opening for the analytical device. The narrowing can be continuous, e.g. conical, or step-wise and the analytical device can be fixed from one or several sides. The narrowing of the chamber can relate to the chamber wall or walls on its entire surface. However, it is also possible that the chamber has one or several elevations on the chamber wall or chamber walls for narrowing which face the chamber interior. The elevations can be shaped identically or differently and for example be present in the form of domes, bars, bulges, ribs or such like. The elevations in the chamber wall have the effect that the analytical element is only partially touched in order to fix its position in the chamber and thus allows an optimization of the forces which result in the fixation.

According to the invention it has turned out to be particularly preferable to fix the analytical devices in the chamber by means of a partially conical narrowing of the chamber wall as well as by means of one or several elevations in the chamber wall. Three ribs particularly preferably serve as elevations which are located on two opposite chamber walls and which slightly bend the analytical device in the chamber and thus fix it in its position by means of the bending stress that is generated. The bending should of course not damage the analytical device or impair the function of the analytical device.

In addition it has turned out to be preferable according to the invention that in each chamber in the storage container according to the invention only one of the at least two openings of the chamber is suitable for loading and removing the analytical devices. Hence only one of the two openings is large enough to remove the analytical device through it or to insert the analytical device into the chamber when loading. This property of the opening is abbreviated in the following to "penetrable to analytical devices".

In the storage containers of the prior art (in particular EP-A 0 738 666 and U.S. Pat. No. 5,510,266), the openings in the bottom surface as well as the openings in the cover surface can be penetrated by the analytical devices contained in the storage container. When loading the storage container with analytical devices according to the said prior art, a surface of the storage container is firstly sealed with a foil and subsequently a number of analytical devices are loaded into the chambers provided therefor. Finally the surface that is still open is also sealed with a foil. The disadvantages of this method are that the first foil can be damaged when the chambers are loaded with the analytical devices and that two manufacturing steps are necessary to seal the chambers. In the preferred storage container according to the invention in which in each case only one of the at least two openings of the chamber can be penetrated by the analytical devices, these disadvantages do not occur. The chambers can be loaded with analytical devices before one of the openings is sealed by a sealing foil since one of the openings of the chamber cannot be penetrated by the analytical devices and thus can serve as the bottom of the chamber on which the inserted analytical device lies. The risk of damaging the foil which does not have to exist in this process step is thus minimized. Furthermore the process of sealing the chambers by foils can be carried out on both sides of the opening simultaneously. Furthermore the sealing foil which is attached to that side of the storage container according to the invention on which the chamber openings that cannot be penetrated by the analytical devices are located, can basically not be damaged or pierced from inside by the analytical device present in the chamber which increases the reliability of the storage container according to the invention.

The removal of the analytical devices from the storage container according to the invention is achieved by pushing the analytical device out of the chamber preferably with the aid of a plunger. For the preferred embodiment of the storage container according to the invention in which one of the two openings of the chamber cannot be penetrated by the analytical device it is preferable that this opening can be penetrated by a plunger which can push the analytical device out of the storage container. It is especially preferred that each chamber has a guide groove for the plunger. This holds the plunger and the analytical device located in the chamber during the ejection process in exactly defined relative positions thus preventing the plunger and analytical element from canting or sliding past one another.

Since the foils which serve to seal the openings of the chambers of the storage container according to the invention must be detachable from the chamber when the analytical device is removed from the chamber, they are naturally a potential mechanical weak point of the storage container according to the invention. Thus the choice of material and thickness of the foil is limited by the fact that it must be possible to tear the sealing foil with the aid of the analytical device in the chamber when the plunger presses against the analytical device. Moreover the analytical device must not be damaged when the foil is torn. In order to protect these sealing foils when for example the storage container is placed on a flat support it has turned out according to the invention to be advantageous to provide elevations on the surfaces of the storage containers that are sealed with foils which prevents direct contact between the foil and support when the storage container is placed on a flat support. These elevations can be designed as a circumferential thin peripheral flange around the outer periphery of the storage container according to the invention. The elevations in the center of the surfaces of the storage container according to the invention sealed with foil have also proven to be advantageous. The elevation can have any desired form, for example, ribs or a plurality of regularly distributed knobs. The height of the elevation essentially depends on the thickness of the sealing foil that is used. In order to be effective according to the invention, the elevation must have at least the thickness of the sealing foil plus the thickness of an adhesive layer that may also be present to fix the sealing foil to the storage container according to the invention. However, the elevation preferably protrudes by at least 300 to 400 µm beyond the surface of the sealing foil. The elevations are preferably not covered with the sealing foil but rather the areas in which the elevations are present are left free. In this case sealing foils are preferably used which are provided with appropriate cut-outs before being mounted on the main body of the storage container. The mounting of such a sealing foil of course requires an exact positioning of the sealing foil relative to the main body of the storage container.

It has proven to be particularly advantageous when at least one of the surfaces of the storage container according to the invention which is provided with a sealing foil is not flat but rather shaped like a cone pointing inwards. This is preferably the surface from which the analytical devices are pushed out of its chamber when the plunger is applied. Of course the opposite surface or both surfaces which are sealed with foil can have this feature. The advantage of the conical shape of the surface is that the sealing foil is protected against unintentional damage since only the external edge can lie on a flat surface. In addition the force which is necessary to tear the foil is reduced by this geometry. The cone is preferably sloped at an angle of 1° to 45° relative to the flat surface, particularly preferably of 1° to 10° and quite especially preferably of 5°.

Appropriate means can be provided in or on the storage container for holding the storage container according to the invention in a measuring instrument and for the automatic removal of individual analytical devices. In this connection it would appear to be important above all to be able to exactly position the storage container relative to the functional components of a measuring instrument and especially relative to the plunger in order to remove the device. Therefore in a preferred embodiment the storage container according to the invention contains a central hole in which a matching guide pin of the measuring instrument can engage. In addition a notch or a gear ring can be present in the hole or separate from the hole into which a corresponding drive device of the measuring instrument can engage in order to move the storage container into a favorable withdrawal position.

In a corresponding measuring instrument a guide pin engages in the central hole of the storage container which holds the storage container in the correct position for removing the devices. For example a drive gear ring can be located on the rim of the central hole into which a correspondingly shaped matching component can engage when the storage container is used in a measuring instrument and with the aid of which the storage container can be rotated in the measuring instrument. The rotation of the storage container in the measuring instrument enables the storage container to be moved into corresponding predefined positions enabling the test elements to be removed from the measuring instrument with the aid of a plunger and making the test elements available for measuring processes.

A further subject matter of the invention is a system for storing analytical devices containing a storage container according to the invention and two or several analytical devices.

The system according to the invention contains a storage container according to the invention as described above. At least two and preferably 10 to 20 analytical devices are located in the storage container each of which is individually sealed in the chamber. The analytical devices are particularly preferably test elements for analyzing liquids e.g. diagnostic test strips or lancets, test elements being quite especially preferred. Of course it is also possible according to the invention to accommodate several types of analytical devices each in their own chambers for example test elements and lancets.

In addition the system according to the invention can contain a compact measuring instrument which can hold the storage container according to the invention with the analytical devices contained therein, preferably test elements, and is able to remove the analytical devices from the storage container. In this process the analytical devices are made available to the measuring instrument in order to carry out the desired analysis.

Finally a subject matter of the invention is a system for storing analytical devices containing one o r several storage containers according to the invention and two or several analytical devices in each storage container in which the storage containers are contained in a container.

In order to additionally protect the analytical devices and the storage containers according to the invention from damaging environmental influences especially humidity, light and mechanical stress, these can be packaged in a surrounding container e.g. a metal or plastic tube that can be sealed with a stopper. This container which surrounds the storage container or containers can preferably contain an additional desiccant and thus increase the storage stability of the analytical devices that are located in the storage containers according to the invention.

The advantages of the invention can be summarized as follows:

The fixing of the analytical devices in the chambers of the storage container protects the sealing foil against unintentional mechanical stress such as when dropped, knocked or shaken.

Fixing the analytical devices in the chambers of the storage container leads to an exact positioning of the devices relative to a plunger with the aid of which they can be pushed out of the chamber. This prevents the plunger from sliding past the device when it is pushed out of the storage container.

The fixing of the analytical devices in the chambers of the storage container also serves as a guide for the devices when they are pushed out of the storage container. This reduces the risk of the devices canting in this process.

Since the opposing chamber openings are preferably designed differently and can thus only be penetrated by the analytical devices on one side, the sealing foil on the surface which cannot be penetrate d by the devices is not en dangered by the content of the chamber when the container is dropped, knocked or shaken; moreover the manufacture is simplified since both surfaces which contain the openings of the chambers can be sealed in one operating step.

The special design of those surfaces of the storage container according to the invention which are sealed with a sealing foil avoids damage to the foil when the storage container is placed on a flat surface. A special design is understood among others to mean that elevations are provided on the surfaces and/or the surfaces are conical and pointing inwards.

A protecting sealing foil also contributes to the protection of the analytical devices in the chambers of the storage container.

Moreover the main body of the storage container according to the invention can be produced cheaply by injection molding of a plastic.

The invention is further elucidated by the following drawings.

DETAILED DESCRIPTION OF THE INVENTION 1 storage container
2 test element
3 test element chamber
4 conically bevelled upper side of the storage container 1
5 sealing foil for the upper side 4
6 elevation on the conically bevelled upper side (4) of the storage container 1
7 desiccant chamber
8 flat underside of the storage container 1
9 elevation on the flat underside 8 of the storage container 1
10 central hole with drive gear ring
11 sealing foil for the underside 8
12 opening for plunger
13 opening for test element removal
14 opening for desiccant loading
15 chamber wall of the test element chamber 3
16 narrowing of the test element chamber 3
17 guide groove for plunger
18 rib-like elevation in the chamber wall 15
19 lancet
20 lancet chamber
21 lancet body
22 tube-shaped container for three storage containers 1
23 stopper for tube-shaped container 22

Figure 1:
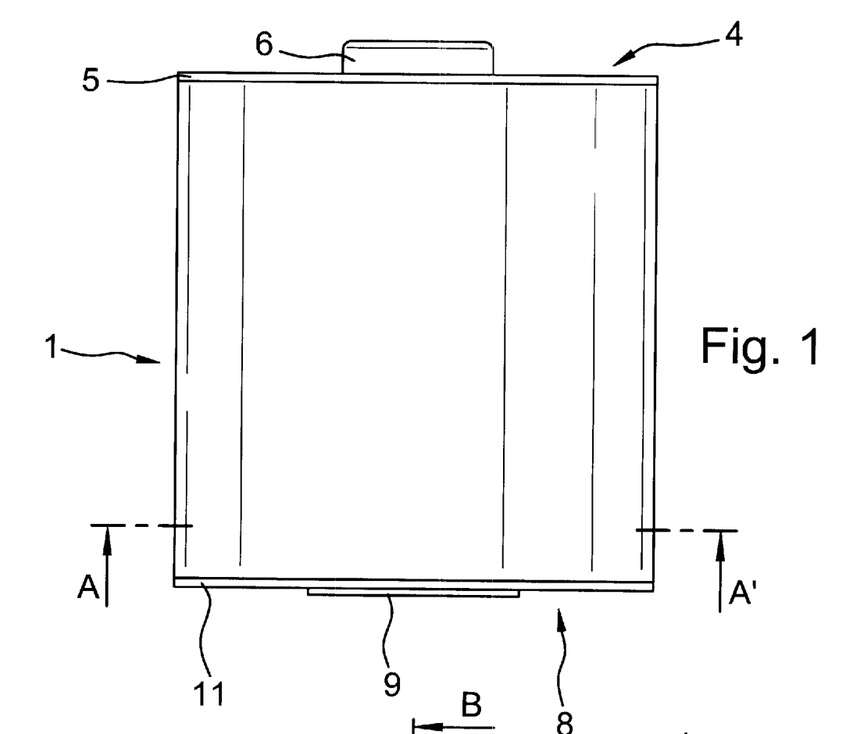
FIG. 1 shows a side view of a preferred embodiment of the storage container according to the invention.

FIG. 1 shows a particularly preferred embodiment of the storage container (1) according to the invention in a side view which in this case is used to store analytical test elements. The storage container (1) is essentially in the form of a cylindrical drum which has a circular conically bevelled upper side (4) and an essentially flat underside (8). The upper side (4) in this case is that side from which the test elements can be removed. The underside (8) is that side through which a plunger can penetrate into the storage container (1) to push out the test elements. The storage container (1) that is shown is preferably made of a rigid injection moldable plastic such as polyethylene or polypropylene. The conically bevelled upper side (4) and the flat underside (8) are provided with sealing foils (5, 11) to protect the analytical test elements contained in the storage container (1). These sealing foils (5, 11) can be glued or welded onto the injection molded main body of the storage container (1). Elevations (6, 9) are provided on the underside (8) of the storage container (1) as well as on the upper side (4) to protect the sealing foils (5, 11). These elevations (6, 9) are preferably a component of the main injection molded body of the storage container (1). They ensure that the sealing foils (5, 11) are not damaged when the storage container (1) is placed on a flat support. The sealing foils (5, 11) have cut-outs in the region of the elevations (6, 9) so that the elevations (6, 9) are not covered by the sealing foils (5, 11).

Figure 2:
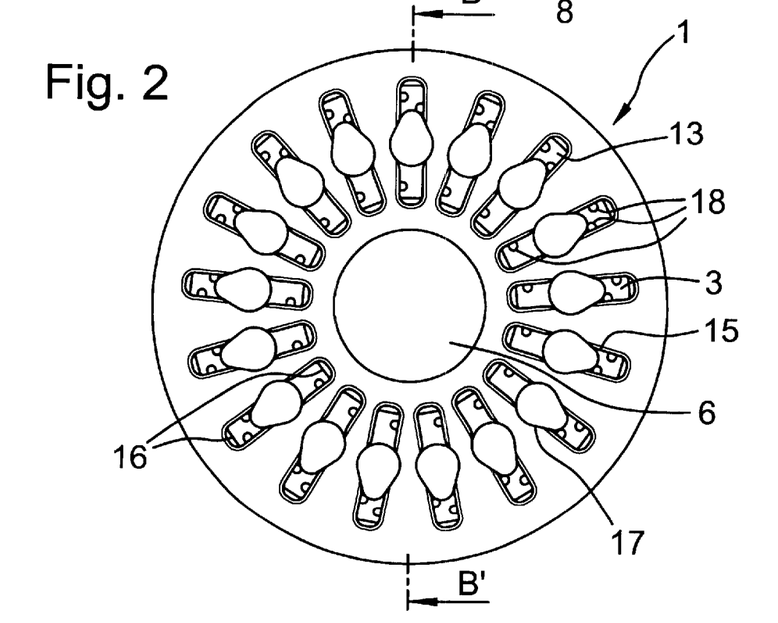
FIG. 2 shows schematically a top view of the circular base surface (cover) of the preferred embodiment of the storage container according to the invention from FIG. 1 in which the sealing foil has been completely removed.

FIG. 2 shows a top view of a conically bevelled upper side (4) of the storage container (1). One can clearly see a plurality of test element chambers (3) which are arranged radially around the elevation (6) of the conically bevelled upper side (4) of the storage container (1). The test element chambers (3) contain the opening for removing test elements (13) on the side facing the conically bevelled upper side (4) of the storage container (1).

Means for fixing the test elements in the test element chamber (3) are provided in the interior of the test element chamber (3). On the one hand a narrowing (16) of the test element chamber (3) is present which can fix a test element present in the chamber from two opposing sides. On the other hand rib-like elevations (18) are located in the chamber wall (15) of each test element chamber (3). Moreover the chamber wall (15) contains a guide groove (17) for a plunger.

Figure 3:
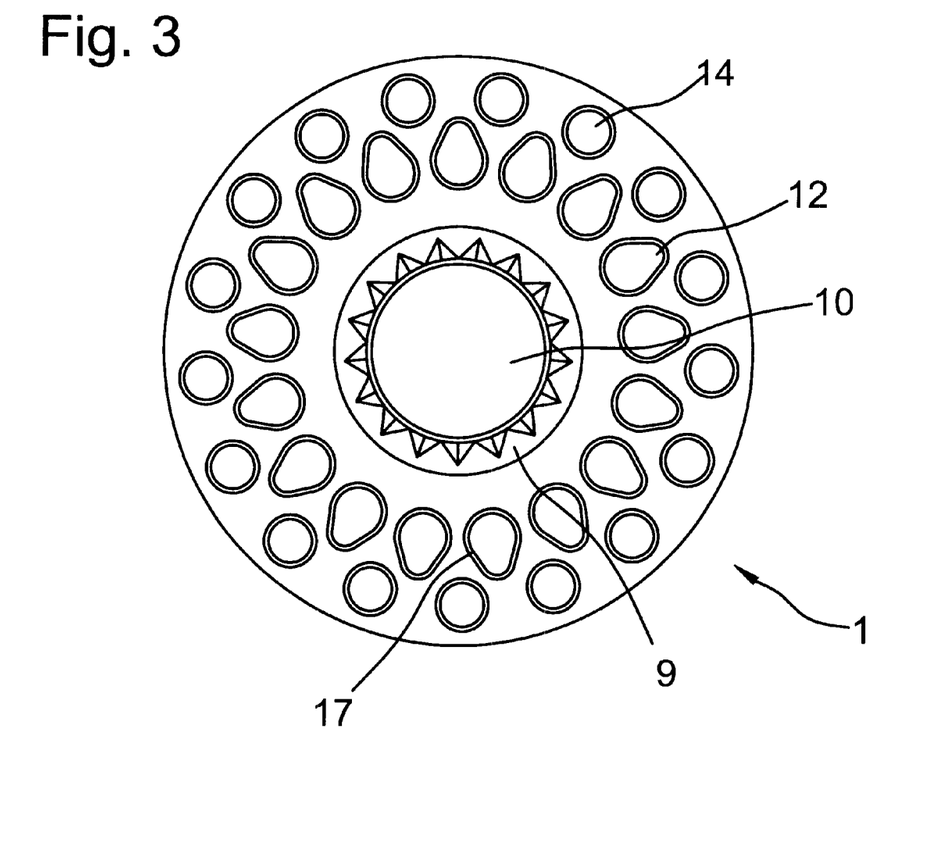
FIG. 3 shows schematically a top view of the circular base surface (bottom) of the preferred embodiment of the storage container according to the invention from FIG. 1 in which the sealing foil has been completely removed.

FIG. 3 shows a top view of the flat underside (8) of the storage container (1) whereby in this case the sealing foil is also removed as in FIG. 2. In this view the openings (12) for a plunger and the opening (14) for filling with desiccant are visible around a central hole (10) with a drive gear wheel which is surrounded by an elevation (9). An opening (12) for a plunger is provided on that side of the test element chamber (3) which faces the flat underside (8) which can be used to push test elements out of the test element chamber (3). The openings (12) for the plunger are connected to the guide groove (17) for the plunger.

The desiccant chambers are linked to the test element chambers via a channel that is not visible in FIG. 3. The dimension of the channel is selected such that individual desiccant particles cannot pass from the desiccant chamber into the test element chamber. However, gas exchange between desiccant chamber and test element chamber must of course be ensured.

Figure 4:
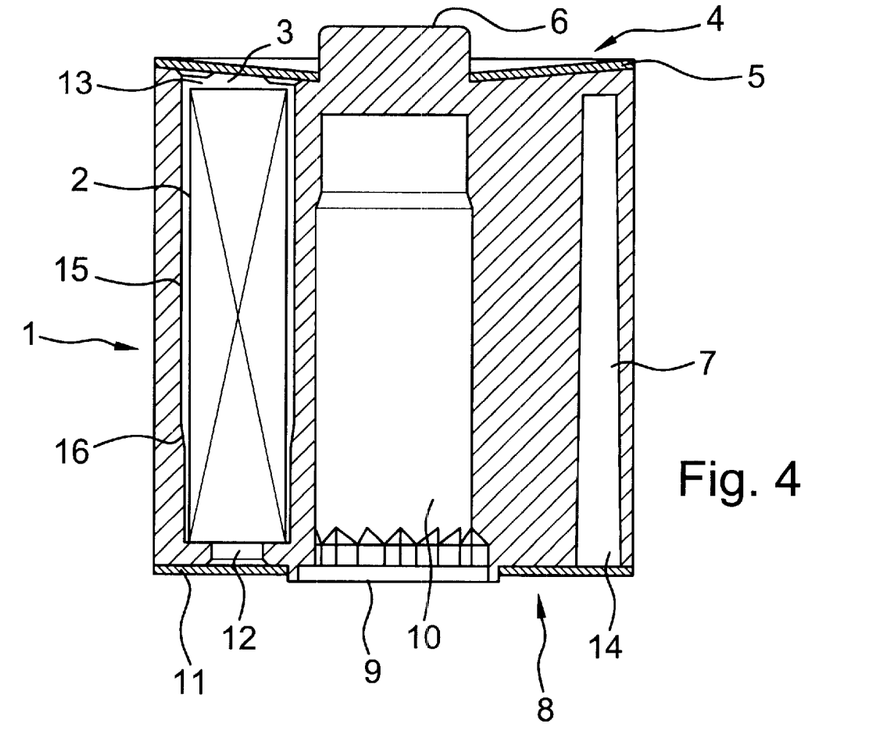
FIG. 4 shows a schematic longitudinal section through a preferred embodiment of the storage container according to the invention from FIG. 1.

FIG. 4 shows a schematic longitudinal section along the line B–B' of the preferred storage container (1) from FIG. 2 according to the invention. The cross-section in particular illustrates the position and shape of a test element chamber (3), a desiccant chamber (7) as well as the central hole (10) with drive gear wheel. Moreover the cross-section from FIG. 4 clearly shows that the upper side (4) of the storage container (1) is conically bevelled. Furthermore a test element C2) is shown schematically in order to illustrate its position in the test element chamber (3).

The test element (2) can be removed from the storage container (1) upwards out of the opening (13) and through the sealing foil (5) of the upper side (4) by a plunger which pierces the sealing foil (11) on the underside (8) and enters the opening (12) provided in the test element chamber (3). The position of the test element (2) is fixed in the storage container (1) by a narrowing (16) as well as by rib-like elevations in the chamber wall (15) in the test element chamber (3). This largely avoids an unintentional piercing of the sealing foil (5) on the upper side of the storage container (1). The sealing foil (11) on the underside (8) of the storage container (1) is protected from piercing by the test element (2) in that the bottom (8) of the storage container (1) only contains one opening (12) for a plunger in the area of the test element chamber (3) through which the test element (2) cannot pass.

The central hole (10) is intended to hold the storage container (1) in a measuring instrument. A guide pin engages in the central hole (10) in a corresponding measuring instrument which holds the storage container (1) in the correct position. The elevation (6) on the conically bevelled upper side (4) of the storage container (1) can also serve to stabilize the position of the storage container (1) in a measuring instrument in addition to the function described above of protecting the sealing foil (5) on the upper side (4) of the storage container (1). The elevation (6) can for example engage there in a matching depression or recess.

A drive gear ring is located on the lower edge of the central hole (10) into which a correspondingly shaped matching component can engage when the storage container (1) is inserted in a measuring instrument and with the aid of which the storage container (1) can be rotated in the measuring instrument. The storage container (1) can be brought into corresponding predefined positions by rotating the storage container (1) in the measuring instrument so that the test elements can be removed from the measuring instrument with the aid of a plunger and the test elements can be made available for measuring processes.

Figure 5:
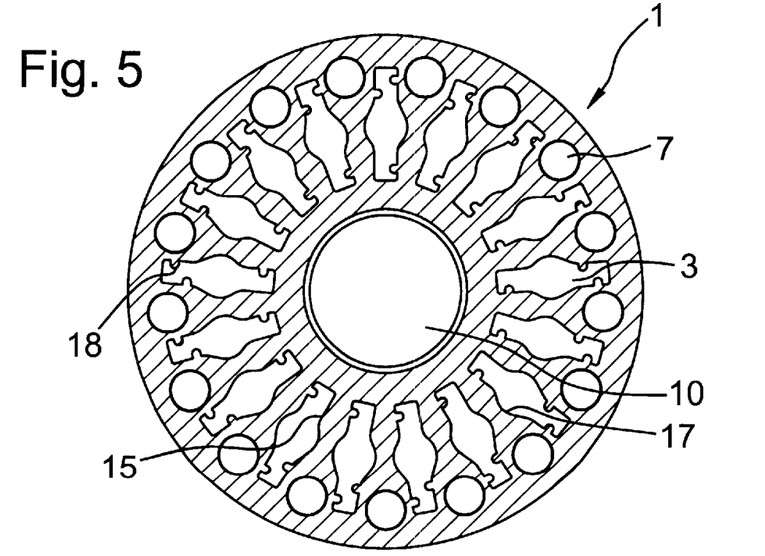
FIG. 5 shows a schematic cross-section through a preferred embodiment of the storage container according to the invention from FIG. 1.

In the particularly preferred embodiment of the storage container according to the invention described here a desiccant chamber (7) which can be filled via an opening (14) with a common desiccant such as silica gel or molecular sieve is located diametrically opposite each test element chamber (3). Each desiccant chamber (7) is allocated a directly adjacent test element chamber (3) and is linked with it via a channel which enables an exchange of air between the desiccant chamber (7) and test element chamber (3). A cross-section along the line A–A' of the particularly preferred storage container (1) according to the invention from FIG. 1 is shown in FIG. 5. This figure shows particularly clearly the rib-like elevations (18) in the chamber wall (15) of the test element chamber (3). Each test element chamber (3) is provided with three such elevations.

Figure 6:
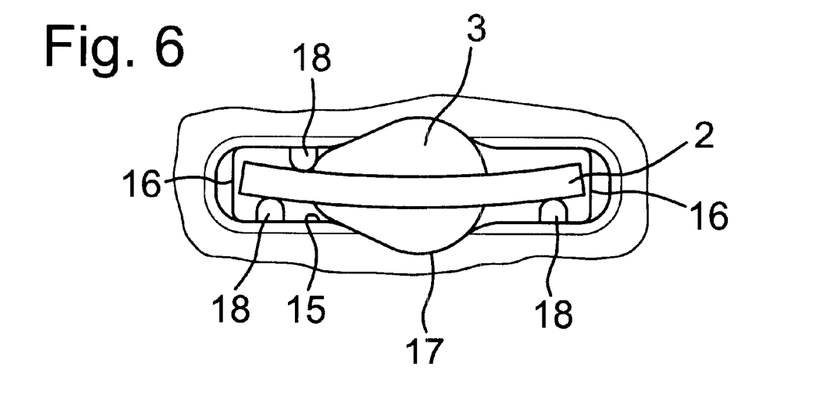
FIG. 6 shows schematically a part enlargement of a test element chamber as shown in FIG. 2 in top view.

FIG. 6 shows an enlarged detailed section of a test element chamber (3) as shown in FIG. 2, in which a test element (2) is fixed in its position with the aid of rib-like elevations (18) in the chamber wall (15) of the test element chamber (3). The rib-like elevations (18) of the chamber wall (15) of the test element chamber (3) ensure that the test element (2) is slightly bent in order to fix it in the test element chamber (3) on the basis of this bending strain. The constrictions (16) of the test element chamber (3) serve to further fix the test element (2). The test element chamber (3) is loaded with the test element (2) by inserting a test element (2) into the chamber (3).

Figure 7:
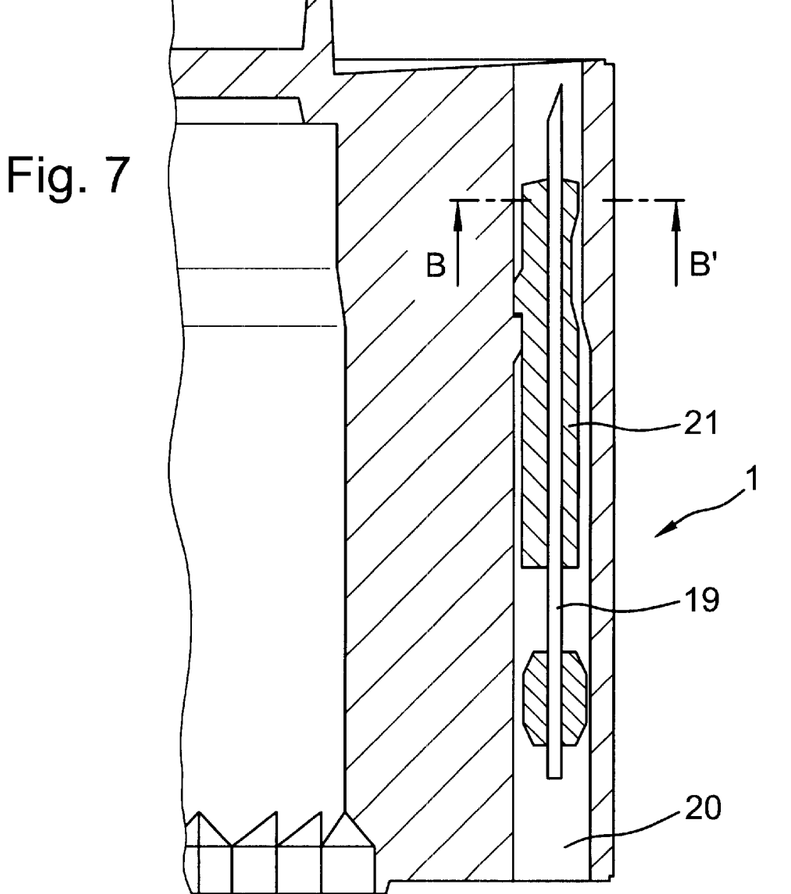
FIG. 7 shows a schematic longitudinal section through a further preferred embodiment of a storage container according to the invention.

FIG. 7 shows a schematic longitudinal section for a further preferred embodiment of the storage container (1) according to the invention. In contrast to the previously described embodiments the embodiment shown in FIG. 7 contains a lancet (19) as an analytical device which is accommodated in a lancet chamber (20). The lancet (19) is partially surrounded by a lancet body (21) made of plastic.

Figure 8:
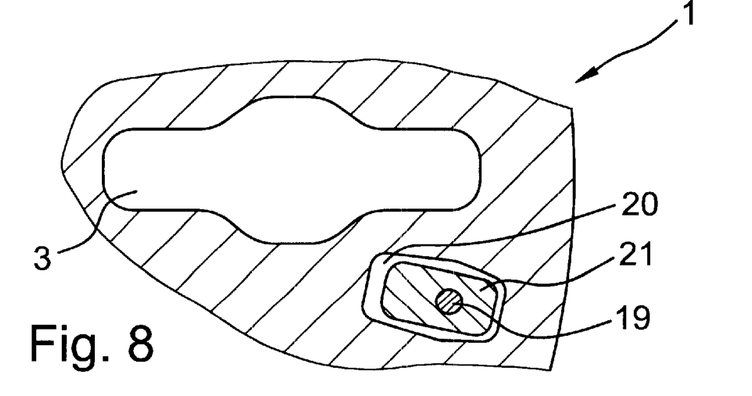
FIG. 8 shows a schematic part enlargement of a cross-section along line B–B' through two chambers of the embodiment of the storage container according to the invention shown in FIG. 7.

As shown in FIG. 8 the storage container (1) according to the invention can also contain a lancet chamber (20) in addition to a test element chamber (3). The test element chamber (3) and lancet chamber (20) can be arranged geometrically in a similar manner to the geometric arrangement of the test element chamber (3) and the desiccant chamber C7) as shown for example in FIG. 5. In addition it is in principle possible to provide desiccant chambers in addition to test element chambers (3) and lancet chambers (20) which are for example in a contact enabling gas exchange with one test element chamber (3) in each case via a channel. It is, however, also possible to not have separate desiccant chambers in the particularly preferred embodiment shown in FIG. 8. For example it is possible to manufacture the inner walls of the test element chambers (3) from a plastic containing desiccant. It is also possible to manufacture the lancet body (21) from a desiccant-containing plastic. In the latter case it is necessary to enable a gas exchange between in each case one test element chamber (3) and a lancet chamber (20) for example by means of a connecting channel.

Figure 9:
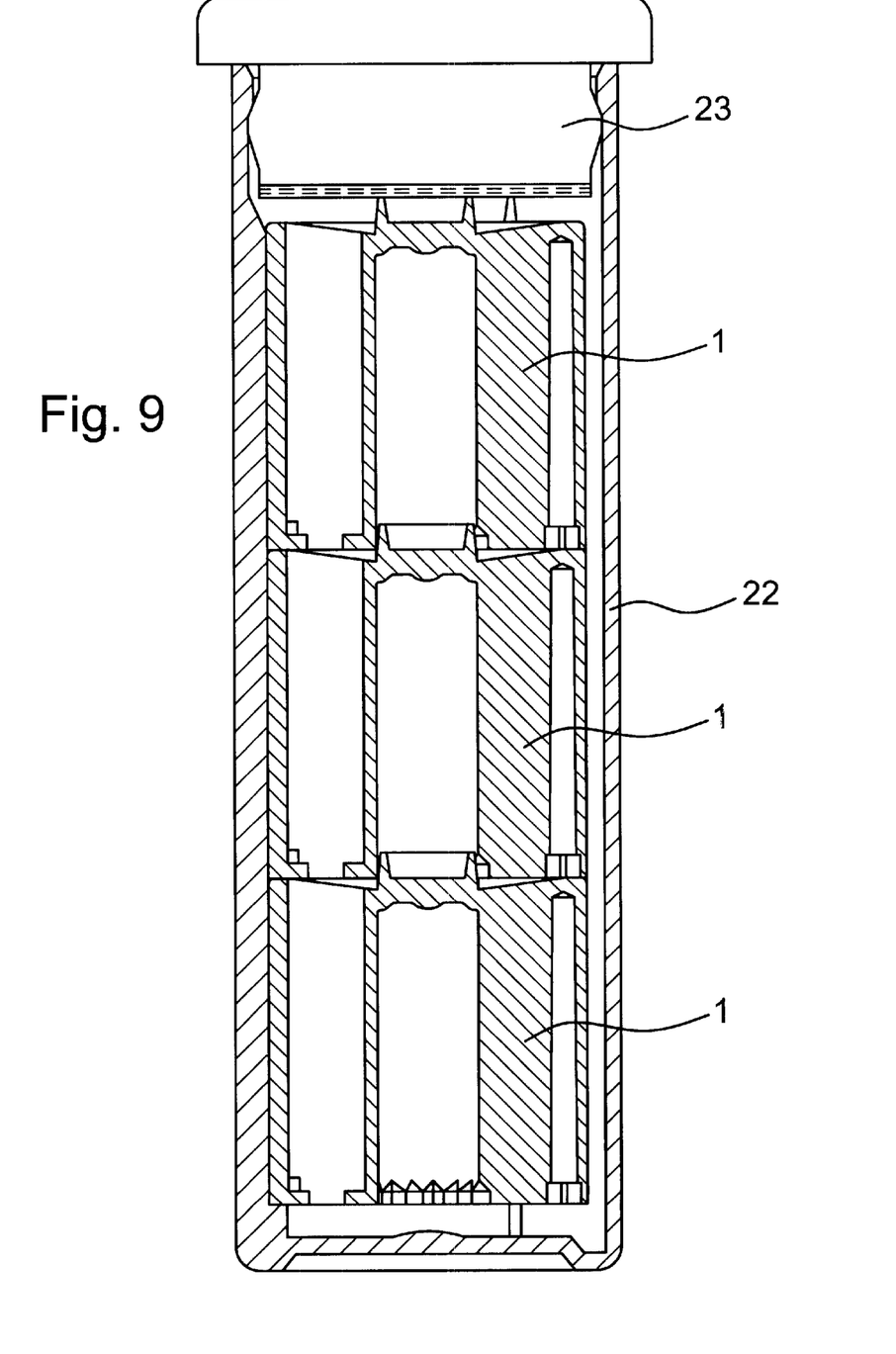
FIG. 9 shows schematically a preferred system according to the invention containing three storage containers for test elements according to the invention and a container for these storage containers in the form of a tube that can be sealed with a stopper.

A preferred system according to the invention is shown schematically in FIG. 9 which in this preferred case is composed of three preferred storage containers (1) according to the invention and a tube-like container (22) that can be sealed with a stopper (23). The system shown in FIG. 9 serves to protect the storage containers (1) according to the invention for example during storage and transport to the end user. The tube-like container (22) is preferably made of a stable, light and moisture impermeable plastic or metal for example polyethylene or polypropylene or aluminium. The stopper (23) is preferably also manufactured from one of the said materials. In the form shown the stopper (23) is simply pressed into the tube (22) thus sealing it tightly. Of course the tube (22) can also be sealed by a screw cap or a hinged closure. An additional desiccant can be provided in the tube-like container (22) to stabilize the test elements contained in the storage containers (1) which is either accommodated at the bottom of the tube-like container (22) or in the stopper (23).

What is claimed is:

1. A storage container for holding analytical devices, the storage container comprising:

a body having an upper side and an under side, the body being formed to include at least one chamber extending between the upper side and the under side, the chamber being defined by a chamber wall extending between a first removal opening at the upper side and a second opening at the under side, the chamber wall narrowing in the region of the chamber which is opposite to the removal opening partially constricting the chamber and including elevations extending into the chamber for engagement with the analytical device, a first foil extending across the upper side, the first foil being formed to seal the first removal opening, and a second foil extending across the under side, the second foil being formed to seal the second opening.

2. The storage container of claim 1 wherein the body is further formed to include at least one desiccant chamber spaced-apart from the at least one chamber.

3. The storage container of claim 1 wherein each of the chambers contains a guide groove extending from the opening at the underside.

4. A storage container for holding analytical devices, the storage container comprising:

a body having an upper side and an under side, the body being formed to include at least one upper elevation extending from the upper side and at least one chamber extending between the upper side and the under side, the chamber being defined by a chamber wall extending between a first opening at the upper side and a second opening at the under side, the chamber wall narrowing in the region of the chamber which is opposite to the first opening partially constricting the chamber and including elevations extending into the chamber for engagement with the analytical device, a first foil extending across the upper side, the first foil being formed to seal the first opening, and a second foil extending across the under side, the second foil being formed to seal the second opening.

5. The storage container of claim 4 wherein the chambers are arranged radially around the elevation.

6. The storage container of claim 4 wherein the upper side is conically beveled.

7. The storage container of claim 4 wherein at least one lower elevation extends from the under side.

* * * * *